United States Patent [19]

Sato, deceased et al.

[11] Patent Number: 5,380,763
[45] Date of Patent: Jan. 10, 1995

[54] TOPICAL COMPOSITION FOR TREATING ACNE VULGARIS

[75] Inventors: Toshiya Sato, deceased, late of Kanagawa, by Kuniko Sato, legal representative; Kenya Ishida, Kanagawa, all of Japan

[73] Assignee: Takasago International Corporation, Tokyo, Japan

[21] Appl. No.: 154,458

[22] Filed: Nov. 19, 1993

[30] Foreign Application Priority Data

Nov. 19, 1992 [JP] Japan .................................. 4-332232

[51] Int. Cl.$^6$ ........................................... A61K 31/045
[52] U.S. Cl. ..................................... 514/724; 514/844; 514/859
[58] Field of Search .................... 514/724, 844, 859

[56] References Cited

U.S. PATENT DOCUMENTS

| | | | |
|---|---|---|---|
| 3,806,593 | 4/1974 | Swanbeck et al. | 424/28 |
| 4,052,515 | 10/1977 | McDermott et al. | 424/343 |
| 4,299,826 | 11/1981 | Luedders | 424/181 |
| 4,657,901 | 4/1987 | Ueda et al. | 514/171 |
| 4,657,935 | 4/1987 | Teplicki | 514/724 |
| 4,678,663 | 7/1987 | Scott et al. | 424/62 |
| 5,096,697 | 3/1992 | Adachi et al. | 424/47 |

FOREIGN PATENT DOCUMENTS

| | | | |
|---|---|---|---|
| 013459 | 7/1980 | European Pat. Off. | A61K 7/48 |
| 0331489 | 9/1989 | European Pat. Off. | A61K 7/48 |
| 60-152415 | 8/1985 | Japan | A61K 31/045 |
| 63-27425 | 2/1988 | Japan | A61K 31/045 |
| 1551637 | 8/1979 | United Kingdom | A61K 7/48 |

OTHER PUBLICATIONS

Adachi et al I CA. 105:11857x (1986) of JP 61 05014 10 Jan. 1986.

Adachi et al. II CA. 104:155727g (1986) of JP 61 15869 23 Jan. 1986.

Adachi et al. III CA 102:137579g (1985) of EP 129778 2 Jan. 1985.

Oono et al. CA 106:201540g (1987) of Ger DE 3522853 2 Jan. 1986.

N. Kato et al., J. Antibact. Antifung. Agents, 8(8), 1–7 (1980).

M. Hattori et al., Chem. Pharm. Bull., 35(8), 3507–3510 (1987).

*Primary Examiner*—Shep K. Rose
*Attorney, Agent, or Firm*—Sughrue, Mion, Zinn, Macpeak & Seas

[57] ABSTRACT

A topical composition for treating acne vulgaris comprising 1-pentadecanol as an active ingredient and a carrier or diluent acceptable for topical composition is disclosed. The composition is highly effective on *Propionibacterium acnes* and of high safety.

3 Claims, No Drawings

TOPICAL COMPOSITION FOR TREATING ACNE VULGARIS

FIELD OF THE INVENTION

This invention relates to a topical composition for treating acne vulgaris, and more particularly to a topical composition which has bactericidal or inhibitory activity on *Propionibacterium acnes*, a pathogenic bacterium causing acne vulgaris, and is markedly effective to treat or prevent acne vulgaris.

BACKGROUND OF THE INVENTION

Acne vulgaris is a skin disease of youths involving comedos, papulae, pustules, etc. appearing on the face, the center of the chest, the upper part of the back, etc. Main causes of acne vulgaris include (1) hypersteatosis, (2) stricture of hair-follicles, and (3) proliferation of *Propionibacterium acnes*, one of Gram positive anaerobic bacteria, in the pilosebaceous gland.

Conventional treatments of acne vulgaris are focused on removal of the above-described three main causes. For example, female hormones are applied to suppression of hypersteatosis; keratolytic substances, e.g., salicylic acid, resorcin, etc. are applied to elimination of stricture of hair-follicles; and bactericidal disinfectants, e.g., Chlorohexidine gluconate, are applied to inhibition the proliferation of the bacterium.

However, conventional bactericidal disinfectants essentially have side effects of causing erythema or exfoliation, thus toughening and irritating skin. It has therefore been difficult to obtain the full effect of such bactericidals due to their limited allowable dose.

In recent years, various naturally occurring substances or synthetic compounds which are antibacterial components safe to the skin have been proposed in the treatment of acne vulgaris. Examples of so-far proposed antibacterial components of natural origin include Ferruginol (see JP-A-1-311018, the term "JP-A" as used herein means an "unexamined published Japanese patent application"), Totarol (see JP-A-1-311019), Sempervirol (see JP-A-1-311020), tetrahydroabietic acid and its esters (see JP-A-2-188513), and anacardic acid (see JP-A-4-36238). 1-Hydroxy-2-pyridone (see U.S. Pat. No. 4,762,847 (1988)) may be mentioned as an example of the synthetic antibacterial component to be used in the treatment of acne vulgaris.

However, since the naturally occurring antibacterial substances are scarce in nature, and the synthetic compounds are not easy to synthesize, both are not easily available and therefore unsatisfactory as an active ingredient for the treatment of acne vulgaris.

1-Pentadecanol, which is the active ingredient of the topical composition for treating acne vulgaris according to the present invention, is a straight chain primary alcohol (1-alkanol) having 15 carbon atoms. In general, 1-alkanols are known to possess antibacterial activity, and it was reported that the effectiveness of 1-alkanols considerably varies depending on the object bacteria (see Nobuyuki Kato, et al., *J. Antibact. Antifung. Agents*, vol. 8, No. 8, pp 1–7 (1980)).

According to this report, a 1-alkanol having 12 or 13 carbon atoms is the most effective on *Staphylococcus aureaus*, one of Gram positive bacteria, among 1-alkanols having 10 to 16 carbon atoms. A 1-Alkanol with 15 carbon atoms has a considerably lesser effect, and that with 16 carbon atoms produces no substantial effect. It is also known that a 1-alkanol with 11 carbon atoms is the most effective on *Aspergillus niger*, which belongs to fungi, and that this antifungal activity is almost lost with an increase of carbon atom number by only one. Further, it was reported that 1-alkanols having 14 to 15 carbon atoms are the most effective against *Streptococcus mutans*, and that one with 16 carbon atoms has substantially no effect (see M. Hattori, et al., *Chem. Pharm. Bull.*, Vol. 35, No. 8, pp 3507–3510 (1987)).

All of the above-mentioned 1-alkanols are on the market and easily available. Some of these 1-alkanols have been confirmed to be safe when applied to the skin and now widely employed as cosmetic bases. For example, lauryl alcohol having 12 carbon atoms (i.e., 1-dodecanol), cetanol having 16 carbon atoms (i.e., 1-hexadecanol), and stearyl alcohol having 18 carbon atoms (i.e., 1-octadecanol) are specified in Standards of Cosmetic Materials edited by Nippon Koteisho Kyokai.

Known formulations of acne vulgaris treating compositions for external use containing a 1-alkanol as a base include a composition comprising benzoyl peroxide as an active ingredient having incorporated therein a primary alcohol having from 6 to 14 carbon atoms for enhancing penetration of the active ingredient into the skin, a diol, and other vehicles (see JP-A-55-120514 corresponding to EP-A-13459), a composition comprising a specific antibiotic, a penetrability improving agent, such as lauryl alcohol, and vehicles, such as ethanol (see JP-A-56-99416 corresponding to U.S. Pat. No. 4,299,826 and EP-A-27286), a composition comprising a specific compound having anti-androkinin activity, an alcohol, such as an aliphatic alcohol having from 1 to 18 carbon atoms, as a solvent and a humectant (see JP-A-61-36219 corresponding to U.S. Pat. No. 4,657,901 and EP-A-138029), a composition excellent in percutaneous absorption and bioavailability comprising an active ingredient, such as benzoyl peroxide, from 20 to 40% by weight of an aliphatic alcohol having from 12 to 22 carbon atoms, volatile silicone as another base, and other additives such as a preservative (see JP-W-61-501091 (the term "JP-W" as used herein means an "unexamined published international patent application") corresponding to U.S. Pat. No. 4,678,663 and EP 172228), a composition containing a lower alcohol, e.g., ethanol, as a compatibilizer between an oily substance and a volatile oil (see JP-A-63-27425), other compositions containing a lower alcohol, e.g., ethanol (JP-A-48-4646 corresponding to U.S. Pat. No. 3,806,593 and GB Patent 1388836 and JP-A-53-94027 corresponding to GB Patent 1551637), and a composition comprising an active agent for killing acne bacteria, a fatty acid and an aliphatic alcohol with the expectation of synergistic effects (see JP-A-2-96522 corresponding to EP Patent 331489).

In all of the above-cited publications, 1-alkanols are described as a base for serving as a solvent, a humectant, an accelerator of percutaneous absorption, and the like in compositions for treating acne vulgaris containing other compounds as active ingredients, with no mention of any effect of the 1-alkanols per se on acne vulgaris.

Formulations containing a 1-alkanol as an active ingredient for treating acne vulgaris are also known. For example, JP-A-60-152415 discloses a composition containing ethanol as a main ingredient exhibiting antibacterial activity on Propionibacterium acnes, and U.S. Pat. No. 4,052,515 proposes a method for treating acne vulgaris comprising applying a combination of a higher alcohol having from 6 to 12 carbon atoms and a lower alcohol to the affected skin and describes the antibacterial activity of the combination against *Corynebacterium acne*. U.S. Pat. No. 4,657,935 teaches gargling with a mixture of water and an alcohol for treatment of acne vulgaris, but the publication does not specify the composition and the effect of the alcohol used.

As aforementioned, various reports on 1-alkanols have been made to date. However, the present inventors find no report on use of 1-pentadecanol as an active ingredient for treating acne vulgaris, still less the antibacterial activity of 1-pentadecanol on *Propionibacterium acnes*.

Use of 1-alkanols containing from 1 up to 22 carbon atoms as a base of acne vulgaris treating agents for external application has already been disclosed, and 1-pentadecanol is included among these alkanols. However, 1-pentadecanol is not so common as a base, and there is found no specific formulation example using 1-pentadecanol.

SUMMARY OF THE INVENTION

An object of the present invention is to provide a topical composition for treating acne vulgaris containing a bactericidal component which is safe to the skin, easily available, and exhibits an excellent effect on acne vulgaris.

In order to accomplish the above object, the present inventors have paid their attention to 1-alkanols which are commonly employed as a base of cosmetics, etc., and are known to be safe to a human body. With the knowledge of antibacterial action of 1-alkanols on several bacteria, such as *Staphylococcus aureaus*, with different antimicrobial spectra, the inventors considered the *Propionibacterium acnes*'s preference for a fatty environment and found that 1-pentadecanol having a longer carbon chain than that of 1-dodecanol, which is the most effective on *Staphylococcus aureaus*, exhibits potent antibacterial activity on *Propionibacterium acnes* while having extremely low toxicity. The present invention has been completed based on this finding.

The present invention relates to a topical composition for treating ache vulgaris containing 1-pentadecanol as an active ingredient.

DETAILED DESCRIPTION OF THE INVENTION

The topical composition for treating acne vulgaris of the present invention can be obtained by formulating 1-pentadecanol as obtained from the market with other components. The lowest effective proportion of 1-pentadecanol in the composition is about 0.005% by weight. A sufficient effect is produced at a proportion of about 0.5% by weight with no need of further increasing the proportion. Accordingly, a suitable proportion of 1-pentadecanol in the composition is from about 0.005 to 0.5% by weight, and preferably from 0.01 to 0.5% by weight.

The topical composition of the present invention can be used as pharmaceuticals, non-pharmaceuticals, cosmetics, sanitary goods, and the like in the form of, for example, beauty lotions, emulsions, creams, masks, aqueous ointments, and oily ointments.

Other components which can be used in the composition for treating acne vulgaris of the invention are appropriately selected according to the dose form from those commonly employed for topical compositions for application to the skin, such as surface active agents, humectants, lower alcohols, water, thickeners, oily bases, ultraviolet absorbents, perfumes, antioxidants, chelating agents, colorants, antiseptics, antifungal agents, and so on. The composition may further contain other active ingredients, such as female hormones and salicylic acid.

Usage of the topical composition for treating acne vulgaris of the present invention is not limited. For example, the composition is preferably applied to the affected part 1 to 3 times a day in proper doses.

The present invention is now illustrated in greater detail by way of Test Examples and Formulation Examples, but the present invention should not be construed as being limited thereto. All the parts are by weight unless otherwise indicated.

TEST EXAMPLE 1

Antibacterial Activity of Active Ingredient

The minimum inhibitory concentration (MIC) of 1-pentadecanol against *Propionibacterium acnes* was determined as follows.

In 1 l of purified water was dissolved 59.0 g of a GAM (Gifu anaerobic medium) bouillon medium (Nissui Pharmaceutical Co., Ltd.) and 1-pentadecanol was added to the bouillon solution to give a concentration of 100 μg/ml. The mixture was stepwise diluted two times with the same medium, followed by sterilization.

A 10 ml aliquot of the mixture was put in a test tube and inoculated with 0.1 ml of the culture of *Propionibacterium acnes* (ATCC 6919) which had been precultured so as to give a cell density of $1 \times 10^8$ cells/ml. The system was static-cultured under anaerobic conditions for 48 hours, and the turbidity was measured at a wavelength of 660 nm to obtain MIC (μg/ml).

For comparison, MIC of 1-dodecanol and 1-hexadecanol, which have relatively strong antibacterial activity on several bacteria and are generally used as a base of cosmetics, against *Propionibacterium acnes* was obtained in the same manner. The results obtained are shown in Table 1 below.

TABLE 1

| Test Compound | MIC (μg/ml) |
| --- | --- |
| 1-pentadecanol | 3.13 |
| 1-dodecanol | 25 |
| 1-hexadecanol | >200 |

As is shown in Table 1, 1-pentadecanol possesses potent antibacterial activity specific to *Propionibacterium acnes* at a far lower concentration than 1-dodecanol whose carbon atom number is smaller than 1-pentadecanol by 3 or 1-hexadecanol whose carbon atom number is greater than 1-pentadecanol by 1.

| Beauty Lotion | |
| --- | --- |
| 1. 1-Pentadecanol | 0.1 part |
| 2. Glycerin | 2.0 parts |
| 3. 1,3-Butylene glycol | 2.0 parts |
| 4. Sodium citrate | 0.1 part |
| 5. Ethanol | 15.0 parts |
| 6. Polyoxyethylene oleyl ether | 0.5 part |
| 7. Methyl p-hydroxybenzoate | 0.1 part |
| 8. Purified water | remainder |
| Total: | 100.0 parts |

Components 1, 5, 6, and 7 were mixed and dissolved at room temperature. Separately, components 2, 3, 4, and 8 were mixed and dissolved at room temperature. The former mixture was added to the latter mixture while stirring to prepare a beauty lotion for treating ache vulgaris.

TEST EXAMPLE 2

Antibacterial Activity of Formulation

Antibacterial activity of the beauty lotion prepared in Formulation Example 1 against *Propionibacterium acnes* was examined as follows.

The beauty lotion was added to 10 ml of a sterilized 5.9% aqueous solution of an GAM bouillon medium (Nissui Pharmaceutical Co., Ltd.) in a test tube to a final concentration of 20 μl/ml or 50 μl/ml. To the test tube was added 0.1 ml of the culture of *Propionibacterium acnes* which had been pre-cultured so as to give a cell density of about $1 \times 10^8$ cells/ml, followed by static-culturing under anaerobic conditions for 48 hours. The turbidity at 660 nm was measured, and the growth of the bacterium was visually observed. For comparison, beauty lotions prepared in the same manner as in Formulation Example 1 except for replacing 1-pentadecanol with 1-dodecanol (Comparative Example 1) or using no active ingredient (Comparative Example 2) were tested in the same manner. The results obtained are shown in Table 2 below. Symbols used in Table 2 have the following meanings.

−: No proliferation of the bacterium being observed, and the culture was clear.

±: Slight proliferation of the bacterium was observed.

+: The culture was turbid with proliferation of the bacterium being observed.

++: The culture was considerably turbid with vigorous proliferation of the bacterium being observed.

TABLE 2

| Formulation | Ingredient | Antibacterial activity 20 μl/ml | 50 μl/ml |
|---|---|---|---|
| Example 1 | 1-pentadecanol | − | − |
| Compara. Example 1 | 1-dodecanol | ± | − |
| Compara. Example 2 | none | ++ | ++ |

As can be seen from Table 2, substantially no proliferation of *Propionibacterium acnes* was observed with the beauty lotion for acne vulgaris according to the present invention as compared with the beauty lotion containing 1-dodecanol or the control containing no active ingredient, proving strong antibacterial activity of the formulation according to the present invention.

FORMULATION EXAMPLE 2

| Cream | |
|---|---|
| 1. 1-Pentadecanol | 0.1 part |
| 2. Dye | 0.003 part |
| 3. 1,3-Butylene glycol | 5.0 parts |
| 4. Bees wax | 2.0 parts |
| 5. Cetanol | 4.0 parts |
| 6. Purified lanolin | 10.0 parts |
| 7. Squalane | 30.0 parts |
| 8. Methyl p-hydroxybenzoate | 0.1 part |
| 9. Polyoxyethylene sorbitan monolaurate | 2.0 parts |
| 10. Purified water | remainder |
| Total: | 100.0 parts |

Component 3 was added to component 10, the mixture was heated, and the resulting aqueous phase was kept at 70° C. Separately, component 1 and other components were mixed and heated at 70° C. to dissolve to prepare an oily phase. The aqueous phase was added to the oily phase, and the mixture was preliminarily emulsified by stirring and then homogenized in a homomixer to obtain an oil-in-water type cream for treating acne vulgaris.

FORMULATION EXAMPLE 3

| Ointment | |
|---|---|
| 1. 1-Pentadecanol | 0.5 part |
| 2. Polyethylene glycol 400 | 10.0 parts |
| 3. Liquid paraffin | 12.5 parts |
| 4. Vaseline | 21.0 parts |
| 5. Paraffin | 7.0 parts |
| 6. Glycerol | 49.0 parts |
| Total: | 100.0 parts |

The above components were thoroughly mixed to prepare an ointment for acne vulgaris.

FORMULATION EXAMPLE 4

| Emulsion | |
|---|---|
| 1. 1-Pentadecanol | 0.1 part |
| 2. Liquid paraffin | 10.0 parts |
| 3. Vaseline | 4.0 parts |
| 4. Stearic acid | 2.0 parts |
| 5. Cetanol | 1.0 part |
| 6. Glyceryl monostearate | 2.0 parts |
| 7. Propylene glycol | 7.0 parts |
| 8. Sodium hydroxide | 0.4 part |
| 9. Purified water | remainder |
| Total: | 100.0 parts |

Components 1 to 6 were mixed, heated to dissolve, and maintained at 70° C. to prepare an oily phase. Other components were mixed, dissolved, and maintained at 70° C. to prepare an aqueous phase. The aqueous phase was added to the oily phase, and the mixture was uniformly emulsified in a homo-mixer, followed by cooling to 30° C. while thoroughly stirring to prepare an emulsion for acne vulgaris.

TEST EXAMPLE 3

Efficacy of Treatment of Acne Vulgaris

Each of the preparations obtained in Formulation Examples 1 to 4 was applied on the right half of the face of five patients having acne vulgaris on their face once in the morning and once in the evening for consecutive 1 month. At the same time, a control preparation having the same composition as the preparation applied to the right half of the face except for containing no active ingredient was applied on the left half of the face in the same manner. At 1 month treatment, the efficacy on acne vulgaris was evaluated by numerically rating the degree of healing on the right half as compared with the left half (control) according to the following rating system and obtaining an average of marks. The results obtained are shown in Table 3 below. Rating System for Evaluation:

4 ... Completely healed.
3 ... Apparently improved.
2 ... Slightly improved.
1 ... No difference from control.

TABLE 4

| Preparation | Marks |
| --- | --- |
| Formulation Example 1 | 3.0 ± 0.7 |
| Formulation Example 2 | 3.3 ± 0.2 |
| Formulation Example 3 | 3.7 ± 0.5 |
| Formulation Example 4 | 3.2 ± 0.3 |

The results of Table 4 obviously prove that the topical compositions for treating acne vulgaris according to the present invention are effective at relatively low doses. In the above clinical testing, no abnormality such as irritation to the skin was not observed.

As described and demonstrated above, the topical composition for treating acne vulgaris according to the present invention which contains 1-pentadecanol as an active ingredient exhibits inhibitory or bactericidal activity on *Propionibacterium acnes*, a pathogenic bacterium causing acne vulgaris, and is effective on treatment of acne vulgaris. The 1-pentadecanol used as an active ingredient has high antibacterial activity at relatively low concentrations and extremely low toxicity so that sufficient effects can be produced at a reduced dose level with high safety. Moreover, 1-pentadecanol obtained from the market can be used as it is.

While the invention has been described in detail and with reference to specific examples thereof, it will be apparent to one skilled in the art that various changes and modifications can be made therein without departing from the spirit and scope thereof.

What is claimed is:

1. A method of treating acne vulgaris cased by *Propionibacterium acnes* which comprises applying to the affected areas of the skin a composition comprising 1-pentadecanol as an active ingredient and a carrier or diluent acceptable for topical composition, wherein said 1-pentadecanol is applied in a concentration effective to inhibit *Propionibacterium acnes*, until the acne is slightly improved, apparently improved and or completely healed.

2. The method according to claim 1, wherein the composition comprises from 0.005 to 0.5% by weight of the active ingredient.

3. The method according to claim 1, wherein the composition comprises from 0.01 to 0.5% by weight of the active ingredient.

* * * * *